United States Patent [19]

Keller

[11] Patent Number: 4,704,354

[45] Date of Patent: Nov. 3, 1987

[54] VIRION ASSAY METHOD FOR USE IN IN VITRO SCREENING OF TERATOGENS AND CARCINOGENS

[75] Inventor: Stephen J. Keller, Cincinnati, Ohio

[73] Assignee: University of Cincinnati, Cincinnati, Ohio

[21] Appl. No.: 580,511

[22] Filed: Feb. 15, 1984

[51] Int. Cl.$^4$ .................. C12Q 1/70; G01N 53/00; G01N 33/533; G01N 21/64; C12N 15/00

[52] U.S. Cl. ........................ 435/5; 435/7; 435/172.1; 250/461.2; 436/546

[58] Field of Search ............... 435/5, 6, 29, 172.1, 435/34, 7; 436/546, 800, 805; 250/461.2

[56] References Cited

U.S. PATENT DOCUMENTS

| | | | |
|---|---|---|---|
| 4,066,510 | 1/1978 | Thilly | 435/6 |
| 4,298,685 | 11/1981 | Parikh et al. | 435/7 |
| 4,299,915 | 11/1981 | Thilly et al. | 435/6 |
| 4,345,026 | 8/1982 | Lew | 435/4 |
| 4,407,942 | 10/1983 | Birnboim | 435/29 X |
| 4,475,236 | 10/1984 | Hoffman | 382/6 |
| 4,492,752 | 1/1985 | Hoffman et al. | 436/805 X |

OTHER PUBLICATIONS

Maggio, Enzyme-Immunoassay, CRC, Boca Raton, 1980, pp. 235-239.

Reynolds, Part V in The Elisa:Enzyme-Linked Immunosorbent Assay in Veterinary Research and Diagnosis, Wardley et al., editors, Martinus Nighoff, Boston, 1982, pp. 112-123.

Keller, S. J. et al, "Animal Virus Screens for Potential Teratogens", *Teratogenesis, Carcinogenesis, and Mutagenesis*, 2:361-374 (1982).

Mackett, M. et al, "Vaccinia Virus: A selectable Eukaryotic Cloning and Expression Vector", *Proc. Natl. Acad. Sci. USA*, vol. 79, pp. 7415-7419, Dec. 1982.

Pienta et al, "Application of Transformation Systems", *Annals of NY Acad. Sci.*, vol. 407 (1983) pp. 267-283, presented Jun. 16, 1983.

J. J. Cornelis et al, "Parvoviral Probe . . . To Human Cells", published in NATO, ASI Series, vol. 60 (1983), Plenum Press-presented at meeting Aug. 24-Sep. 5, 1981, in Pisa, Italy, pp. 119-140.

D. Panicali et al, "Construction of Live Vaccines . . . Virus Hemagglutinin", *Proc. Natl. Acad. Sci. USA*, vol. 80, pp. 5364-5368, Sep. 1983.

*Primary Examiner*—David M. Naff
*Assistant Examiner*—Shawn P. Foley
*Attorney, Agent, or Firm*—Wood, Herron & Evans

[57] ABSTRACT

A cytofluorograph is used to quantify poxvirus concentration. Virions producing a known cell bound antigen are added to a cell culture. The antigen is fluorescently labeled and the infected cells are counted cytofluorographically. Certain mutated virions do not produce the labeled antigen and are not counted. Alternately, the virion infected cell culture is stained with a phenanthridium dye. Only infected cells absorb the dye. Dead cells are counted with a cytofluorograph indicating virion concentration. The two tests combined discriminate between teratogens and carcinogens. Toxins which are teratogens reduce the number of infective virus, whereas carcinogens not only reduce the virus number, but increase the number of mutants.

4 Claims, No Drawings

VIRION ASSAY METHOD FOR USE IN IN VITRO SCREENING OF TERATOGENS AND CARCINOGENS

BACKGROUND OF THE INVENTION

The detection of potential human toxins traditionally has relied upon in vivo methods using large numbers of suitable laboratory animals, such as mice, hamsters, rabbits and monkeys. In vivo testing using laboratory animals is extremely expensive, and the length of time required to conduct useful in vivo studies is excessive. Considering the ever increasing number of new chemicals introduced each year, these problems are compounded. A suitable testing system should be capable of assaying 2,000 new compounds each year. In vivo methods are simply too expensive and time consuming to be used.

In addition, in vivo methods are not always reliable. For example, in vivo tests indicated that thalidimide was inactive in mice at 4,000 mg/kg. Unfortunately, it was later found to cause birth defects in humans at 0.5 mg/kg.

Primarily due to expense and time consumption, many in vitro methods have been developed. These include gene tox tests such as Ames assays, sister chromatatid exchange, unscheduled DNA synthesis and growth of cell cultures. More recent teratogen tests have included the Braun cell adhesion assay, hydra-aggregation, cell culture differentiation and the Virus Assay.

The major limitation of model systems is that they oversimplify the complexity of a multi-cellular organism. This point is most obvious for the Ames gene tox test that has a requirement for a liver cell-free supernatant to activate potential mutagens. The difficulty in producing uniformly active extracts has contributed to the wide variability that has been observed for Ames testing from lab to lab. Although animal cell cultures have the appropriate biochemical background to activate or inactivate potential toxins, these cells usually have chromosomal and developmental abnormalities.

In principle, a model system for human toxins should test both genetic continuity and the ability of an organism to direct that information into a complete developmental sequence. The ideal model should be easily grown in a laboratory, utilize mammalian metabolic pathways, including those in different tissues and the developing embryo, proceed through a developmental sequence in a short period of time, produce a large number of adults that are characterized by quantitative endpoints, be analyzable for genetic continuity, and be analyzable at the biochemical level in order to confirm the activity of the suspected toxin.

One such teratogen assay method is based on the ability of primate derived cell cultures to support infection by poxvirus. The assay uses as an endpoint the number of active progeny virions released from an infected cell that has been treated with a toxin (hereinafter referred to as the virion progeny assay method). Untreated but infected cell cultures and uninfected cell cultures serve as controls. The rationale behind using such a model to predict toxicity is twofold. First, the virus will undergo reproduction only if allowed to infect a cell that is in an active state of proliferation. Since pox virions such as vaccinia take over all of the cell's biochemical machinery as metabolites, enzymes and ribosomes, the number of progeny virions produced in a cell is very sensitive to the cell's general state of health. Thus, any toxin that acts by inhibiting cell proliferation or by disturbing the host metabolism in subtle ways that may not be overtly or immediately cytotoxic will cause a quantitative change in the number of virions.

The endpoint measurement reflects direct interference with either the virion's ability to carry out its macromolecular synthesis or the virion's ability to carry out its morphogenesis.

Using the virion progeny assay method, a toxin can be characterized by a constant, RD50. The RD50 is a concentration of toxin that is necessary to inhibit production of virus 50%. The concentration that inhibits the number in vitro is very close to the concentration of toxin that is active in vivo. There is a positive co-relationship when RD50 dosages are compared to the in vivo LTD's (lowest teratogenic dose).

The virion progeny assay method provides several advantages. This test can be used with selected mammalian cells. Accordingly, the toxicity of a chemical can be tested with respect to many specific types of mammalian cell including liver, embryo, kidney and the like. Further, this method is relatively rapid and very reliable if performed carefully in a quality virus lab. This test also provides RD50 for different concentrations of toxin. The RD50 provides an easily identifiable endpoint and a reliable prognostication of teratogenicity.

The problem encountered with this method of testing is the quantification of virion progeny. One known method of determining virion concentration is to infect a cell culture with a virion-containing test solution and comparing that cell culture with a cell culture which is not infected. In other words, a plaque assay method. This plaque assay method is described in Poxvirus Morphogenesis Screens by Keller and Smith, a paper first presented at the FDA-EPA workshop on in vitro teratogens and later at the Gordon Conference. The plaque assay method is the weak link in using the virion progeny assay method. The plaque assay requires a virus lab and extreme care in producing reliable results. A plaque assay method, like the Ames test, will lack reproducability due to a lack of uniformity in the methodology.

SUMMARY OF THE INVENTION

The present invention is premised upon the realization that viable virion progeny can be quantified from a test solution by infecting a cell culture with the virion progeny fluorescently labeling infected cells and employing a cytofluorograph to identify the number of infected cells. In one embodiment, a virus producing a known antigen is detected. Specifically, the antigen is a cell-bound antigen. The antigen, and thus the infected cell, can be fluorescently labeled using a fluorescent antibody specific to the produced antigen. In a second specific embodiment, the individual infected cells can be counted using a cytofluorograph wherein the cell culture is treated with a phenanthridium dye which is absorbed only by infected cells.

Measuring labeled antibody indicates the number of cells infected with non-mutated virions. Measuring the infected cells which have absorbed the phenanthridium dye indicates the number of cells infected with both mutated and non-mutated virions. Thus, by combining both methods, one can determine the number of virions present in a test solution and ascertain the number of mutant, but active, virions present.

This method is vastly superior to a plaque assay method because it is simple, quick, reliable and provides a direct method of counting viable virions. By careful selection of the virion, much can be learned about the particular toxin employed and how it affects the virus and the selected cells. These and other advantages will be appreciated in light of the following detailed description.

DETAILED DESCRIPTION

Progeny Assay Method

Monolayers of selected cells are synchronously infected with a poxvirus at a low multiplicity of infection, i.e., 0.1 to 1 MOI. Once the virus has been absorbed, the infected cells are then suspended in complete media containing various dosages of the toxin being assayed. Uninfected and untreated cells serve as controls. The poxvirus replicates within the infected cell, but is not released until the infected cell is lysed. After 24 hours of infection, the infected plates are washed, suspended in hypotonic media and frozen at $-80°$ C. The uninfected plates are examined microscopically and stained with trypan blue to determine viability.

The progeny virion is titered from infected cell extract. Serial dilutions of the progeny virions are infected on cell cultures, such as HeLa spinner cultures. At limiting dilutions, only one poxvirus will infect any one cell. If there were, for example, six concentrations of toxin, three serial dilutions of virus, and two uninfected controls, a total of 20 samples will be necessary for one analysis. The number of infected cells must then be determined as well as the number of mutant virus.

For use in the present invention, the virus is a poxvirus, preferably vaccinia. This poxvirus will undergo reproduction only if allowed to infect a cell that is already in an active state of proliferation. Since a poxvirus takes over all of the cell's biochemical machinery as metabolites, enzymes and ribosomes, the number of progeny virions produced in a cell is very sensitive to the cell's general state of health. Thus, any teratogen that acts by inhibiting cell proliferation or by disturbing cell metabolism in subtle ways that may not be overtly or immediately cytotoxic will cause a quantitative or qualitative change in progeny virions.

Further, the vaccinia virus undergoes a specific sequence of steps that may be considered as a developmental pathway, from the time the parental virions are adsorbed to the host cell until the release of the progeny virions. Each of the stages of viral development has been well described at the microscopic and biochemical level. The endpoint measurement reflects direct interference with the virion's ability to uncoat itself in the cytoplasm, translate its messages, replicate its DNA, assemble its chromosome, synthesize its protein core or lipoprotein membrane and complete its morphogenic pattern.

For example, a suitable virus is recombinant vaccinia VP53 which contains the influenza HA gene that has been inserted into the Hind III F portion of the viral genome. The influenza hemagglutinin is a very well characterized antigen for which antisera is commercially available. For example, the antisera is sold by Flow Labs of McLean, Virginia. In addition, the method of making this antisera, and even a biotinylated or labeled antisera is well known to those of ordinary skill in the art.

DETECTION OF VIRAL INFECTED CELLS

When the virus is vaccinia VP53 containing influenza HA gene inserted in the Hind III F portion of the viral genome, the cells infected with progeny virions are detected by detecting the influenza hemagglutinin surface protein using a cytofluorograph. Moreover, the expression of influenza hemagglutinin gene occurs early during infection, and the antigen is inserted into the infected cell's membrane. Thus, infected cells will express a surface antigen that is not expressed in uninfected cells or cells infected with mutant virions. The antigen can be identified by specific fluorescently labeled antisera. The antisera can be biotinylated antisera or a second antibody specific to this antisera and which is conjugated to biotin can be added to the cell culture. Such an antibody can be purchased from Vector Labs. The resulting complex is stained by the addition of avidinfluorescein. This system preserves the initial recognition of the virus antigen, but amplifies the number of fluorescein molecules approximately ten times over the fluorescent anti- sera.

The quantitation of fluorescent cells (infected) is accomplished with a cytofluorograph. The cytofluorograph detects fluorescence of individual cells. For example, a FACS IV cytofluorograph made by Becton Dickinson can be used. This instrument is equipped with a mercury arc lamp that is useful with most of the known dye systems, such as FITC rhodamine, Hoechst, propidium iodide and phycoerythrin. 30,000 FITC molecules per cell can be detected by the fluorescence, and 1.6 micron surface volumes can be detected by scatter. Moreover, the instrument includes a dedicated computer and software for data storage, analysis that will yield the percent of the fluorescent cells directly. A single titration of 20,000 cells should take a minute if the sample density is 5 x 10E6. The best time for the titration of influenza HA antigen is 5 to 6 hours post-infection.

Wild vaccinia infection also produces its own set of surface antigens. Thus, it is also possible to use the wild type virion and labeled antisera that has been produced after vaccination of rabbits or mice.

The detection of both the influenza HA and a second vaccinia encoded surface antigen permits double labeling of the infected cells. Each antigen can be distinctly labeled with different colors, and can be distinguished by the cell sorter. If the mutation inactivates only the portion of the DNA containing one of these genes, one can identify the cite of activity of the toxin.

Infected cells can be recognized late, post-infection using a non-antigenic technique as well. Live uninfected cells do not incorporate certain dyes such as phenanthridium-type dyes such as ethidium bromide, or propidium iodide. On the other hand, 99% of the cells that are virally infected for more than 24 hours may be stained. Since phenanthridium dyes have strong fluorescent signals, infected and uninfected cells can be quantified using the cytofluorograph cell analyzer system, such as the FACS system. Infected cells preferably are subjected to this staining and a fluorescently labeled antisera providing two or three separate means to measure viral infec- tion.

This multi-step method of determining viral infection is very significant. There are two explanations for producing less virus in the presence of toxin: one, the toxin causes genetic damage to the virus; or two, the toxin interferes with the development of the virus. Measuring expression of one or more viral genes enables one to distinguish between these two possibilities. The detected genes are not essential for the functioning of the virus. If the virus has been genetically damaged, i.e., is a mutant, then some of the infected cells will no longer be positive for those detected genes. The cells infected with mutant genes will take up the phenanthridium dye. If no genetic damage or mutation has occurred, all the virus that have been exposed to the toxin will express these genes and also take up the phenanthridium dye. For example, when the virus is vaccinia VP53, the influenza HA antigen can be detected at the same time the phenanthridium dye is detected. This is possible since infectivity is measured by red fluorescence, i.e., phenanthridium dye measurement, and influenza HA antigen by green fluorescence.

In this example, three things can occur when a virus infected cell is contacted with a potential toxin. If the toxin is not harmful, the virus will multiply, and a greater number of viral infected cells (red fluorescing cells) will be produced, each cell showing or expressing the genetic material of the virus (green fluorescing cells).

The second possibility is that the toxin will prevent viral multiplication, and thus there will be fewer viral progeny to infect the cells. In such a situation, fewer viral infected cells (red) will be detected, and the number of red cells detected will equal the number of green cells detected indicating no mutation.

A third possibility is that the toxin will cause mutation of the virus. In this situation, fewer green cells will be detected than red cells. Since the HA gene is located at a known portion of the vaccinia DNA, it can be assumed that the toxin causes mutation in that portion of the genome. By detecting other antigens produced at other portions of the viral DNA, one can map out the sites at which the toxin causes mutation. In turn, this provides greater understanding of the toxin's mechanism of operation. Thus, by detecting gene expression of the mapped virus, one can understand the site of activity of the toxin, and thus better understand its mode of operation.

More generally, by detecting surface-active antigens, one can rapidly and accurately detect viral infection, and thus quantify viral concentration of an unknown solution. This, in turn, provides a means to rapidly detect teratogenicity or carcinogenicity of various toxins at various concentrations for selected cells. In addition, detecting viral infected cells by measuring or detecting cells which have uptaken a phenanthridium dye also provides a direct quantitative method of determining viral concentration in an unknown solution. Again, this provides a direct means to determine teratogenicity of various concentrations of various toxins.

In light of the foregoing description, I claim:

1. The method testing the teratogenicity and carcinogenicity of a chemical comprising:

adding a known concentration of said chemical to a concentration of selected mammalian cells to form a test cell solution;

adding a known quantity of vaccinia virions to said test cell solution;

culturing said virions in said test cell solution whereby said virions are permitted to infect said cells and reproduce to produce progeny virions;

subsequently isolating a solution containing said progeny virions from said test cell solution;

adding a known quantity of said solution containing said progeny virions to a second cell culture and permitting said progeny virions to infect the cells in said second cell culture, whereby infected cells in said cell culture produce a cell bound antigen;

detecting the number of antigen-containing cells;

detecting the number of virally infected cells and relating the number of detected antigen-containing cells and the number of virally infected cells to the carcinogenicity and teratogenicity, respectively, of the chemical.

2. The method claimed in claim 1 wherein said antigen is labeled with a compound detectable by a cytofluorograph and further comprising detecting said labeled antigen by means of a cytofluorograph.

3. The method claimed in claim 1 wherein said vaccinia is vaccinia VP53 and said antigen is produced by influenza HA gene.

4. The method claimed in claim 1 comprising adding a phenanthridium dye to said virally infected cells in said second cell culture whereby said dye is absorbed only by said virally infected cells.

* * * * *